United States Patent
Jin et al.

(10) Patent No.: US 11,058,740 B2
(45) Date of Patent: Jul. 13, 2021

(54) **COMPOSITION FOR PREVENTING, ALLEVIATING OR TREATING STRESS DISEASES, CONTAINING *PLATYCODON GRANDIFLORUM* EXTRACT AS ACTIVE INGREDIENT**

(71) Applicant: SUNG KYUN BIOTECH CO., LTD., Gyeonggi-do (KR)

(72) Inventors: Mi Rim Jin, Seoul (KR); Do Heon Lee, Daejeon (KR); Sun Yeou Kim, Seoul (KR)

(73) Assignee: SUNG KYUN BIOTECH CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/605,677

(22) PCT Filed: Apr. 18, 2018

(86) PCT No.: PCT/KR2018/004497
§ 371 (c)(1),
(2) Date: Oct. 16, 2019

(87) PCT Pub. No.: WO2018/194370
PCT Pub. Date: Oct. 25, 2018

(65) Prior Publication Data
US 2020/0113962 A1    Apr. 16, 2020

(30) Foreign Application Priority Data
Apr. 18, 2017  (KR) .................. 10-2017-0050037

(51) Int. Cl.
*A61K 36/752* (2006.01)
*A23L 33/105* (2016.01)
*A61P 25/24* (2006.01)
*A61K 36/346* (2006.01)

(52) U.S. Cl.
CPC .......... *A61K 36/752* (2013.01); *A23L 33/105* (2016.08); *A61K 36/346* (2013.01); *A61P 25/24* (2018.01); *A23V 2002/00* (2013.01)

(58) Field of Classification Search
None
See application file for complete search history.

(56) References Cited

U.S. PATENT DOCUMENTS 5,589,182 A * 12/1996 Tashiro ................ A61K 36/232
424/423

FOREIGN PATENT DOCUMENTS

| CN | 101229267 A | * | 7/2008 |
| CN | 102274423 A | * | 12/2011 |
| CN | 103100035 A | * | 5/2013 |
| JP | 2004083449 | | 3/2004 |
| KR | 20020022342 | | 3/2002 |
| KR | 20110138082 | | 12/2011 |
| KR | 1020120131970 | | 12/2012 |
| KR | 101386791 | | 4/2014 |
| KR | 1014934730000 | | 2/2015 |

OTHER PUBLICATIONS

Choi (Journal of Ethnopharmacology (2017), vol. 196, pp. 141-150—available online Dec. 14, 2016).*
Song et al., "Effect of Platycodon grandiflorum Extract Intake on Fatigue Reduction by Meridian Massage", Kor. J. Aesthet. Cosmetol., vol. 13, No. 1, Feb. 2015, pp. 75-83.

* cited by examiner

*Primary Examiner* — Susan Hoffman
(74) *Attorney, Agent, or Firm* — Duane Morris LLP; Gregory M. Lefkowitz; Brandon A. Chan (57) ABSTRACT

The present disclosure relates to a composition for preventing, alleviating or treating stress diseases, containing a *Platycodon grandiflorum* extract as an active ingredient, and, more specifically, to a food composition for preventing or alleviating stress diseases or a pharmaceutical composition for preventing and treating stress diseases, both of which contain a *Platycodon grandiflorum* extract and a *Citrus aurantium* extract as active ingredients. A method of the present disclosure can be used for the preparation of an agent for treating depression and anxiety, which are stress diseases, with few side effects because of the use of a natural material, and a health functional food having effects of alleviating depression, anxiety and fatigue, which are stress diseases.

4 Claims, 9 Drawing Sheets

COMPOSITION FOR PREVENTING, ALLEVIATING OR TREATING STRESS DISEASES, CONTAINING *PLATYCODON GRANDIFLORUM* EXTRACT AS ACTIVE INGREDIENT

CROSS-REFERENCE TO RELATED APPLICATIONS

This application is a § 371 national stage entry of International Application No. PCT/KR2018/004497, filed on Apr. 18, 2018, which claims priority to Korean Patent Application No. 10-2017-0050037, filed Apr. 18, 2017, the entire contents of which are incorporated herein by reference.

TECHNICAL FIELD

This application claims the priority of Korean Patent Application No. 10-2017-0050037, filed on Apr. 18, 2017, the entire contents of which are herein incorporated by reference.

The present disclosure relates to a composition for preventing, alleviating or treating stress diseases, containing a *Platycodon grandiflorum* extract as an active ingredient, and, more specifically, to a food composition for preventing or alleviating stress diseases or a pharmaceutical composition for preventing and treating stress diseases, containing a *Platycodon grandiflorum* extract as an active ingredient.

BACKGROUND ART

Depression occurs as the amount of specific neurotransmitters is decreased in the brain. Typical neurotransmitters are serotonin, norepinephrine and corticosterone. Therefore, therapeutic agents for depression exhibit therapeutic effect by increasing the amount of these neurotransmitters in the brain. In the past, imipramine, amitriptyline, trazodone, etc. have been mainly used as antidepressants. Although these drugs are frequently used in clinical applications due to good therapeutic effect, they cause side effects such as constipation, dry mouth, sleepiness, etc. because they block neurotransmitter receptors such as acetylcholine, histamine, etc. Recently developed antidepressants have minimized these side effects to such an extent that the patients hardly feel inconvenience during medication. The representative drugs include Prozac, Zoloft, Seroxat, Dumirox, etc. These drugs selectively increase the amount of serotonin among the neurotransmitters. The most recently developed drugs are similar in action to the previous antidepressants but are improved remarkably in terms of side effects.

It is known that excessive and lasting stress causes depression, anxiety and fatigue, and is related with the increased level of cortisol, which is a stress hormone. Cortisol restores the energy of the body and the mind from stress and regulates blood pressure. However, repeated stress sustains the secretion of cortisol, ultimately leading to depression, anxiety and fatigue by inducing decline in neuroplasticity through negative feedback regulation of the hypothalamic-pituitary-adrenal (HPA) axis.

The treatment of depression is emerging as an important social issue. According to a report by Dr. Lopez of the World Health Organization (WHO), when diseases are ranked based on the concept of disability-adjusted life year (DALY), or 'the number of lost years of healthy life', it is expected that depression will rank 2nd in 2020 following ischemic heart disease. The number of patients is increasing quickly and it is expected that depression will rank 1st in developed countries. Although there are various hypotheses about the biological cause of depression, the dominant view sees it as the disorder of brain neurotransmitter systems such as adrenaline, dopamine, serotonin, etc. at present. It is mainly presumed from the action of the therapeutic drugs, tricyclic antidepressants (TCAs) and selective serotonin reuptake inhibitor (SSRIs). The SSRIs, which are used the most frequently at present, show no significant difference from the TCAs in effect. Another important aspect is that the problem of drug interaction is serious. In particular, because the proportion of poor metabolizers is 4 times or higher in Koreans than in Westerners, toxicity may cause problems. Therefore, new antidepressants suitable to the constitution of Koreans are necessary.

In Korea, some antidepressants based on herb medicine are available on the market. As a typical example, "Jarsin" is an antidepressant marketed since August 1999. Its main ingredient is U160 extracted from the plant St. John's wort (*Hypericum perforatum*). This plant has been used in folk medicine in Britain. It effectively treats the physical symptoms accompanied by depression such as gloom, anxiety, insomnia, etc. and is known be relatively safe. This drug has been prescribed in Germany about 6 times more than fluoxetine. When compared with the existing antidepressants in effect, there are inconsistent reports stating that its response rate is 6-18% times lower than tricyclic antidepressants and that it exhibits at least the same effect as the SSRI sertraline in outpatients with mild to moderate depression. It seems that more studies are required. However, the users of complementary/alternative medicine including herb medicine are close to 40% of the whole population. Even the mainstream North American psychiatry acknowledges the efficacy of new antidepressants with herb medicine as major ingredients together with the use of ginkgo in the treatment of dementia.

With regard to therapeutic agents for depression using natural products, a mixture of rhizoma cyperi, *Poria cocos* Wolf, licorice and barberry root is known to be effective for depression (Korean Patent Publication No. 10-2012-0130973), and a patent filed by the inventors of the present disclosure states that a mixture of rhizoma cyperi, linderae radix, elecampane, licorice, *Platycodon grandiflorum* and *Citrus aurantium* is effective for depression (Korean Patent Registration No. 10-1386791). However, nothing is known about the therapeutic effect of an extract of *Platycodon grandiflorum* alone for depression.

DISCLOSURE

Technical Problem

The inventors of the present disclosure have conducted experiments for investigating the effect of extracts of various natural products on depression, and have completed the present disclosure by identifying that a *Platycodon grandiflorum* extract is effective for treatment of depression.

The present disclosure is directed to providing a food composition for preventing or alleviating stress diseases, which contains a *Platycodon grandiflorum* extract as an active ingredient.

The present disclosure is also directed to providing a food composition for preventing or alleviating stress diseases, which consists of a *Platycodon grandiflorum* extract.

The present disclosure is also directed to providing a food composition for preventing or alleviating stress diseases, which consists essentially of a *Platycodon grandiflorum* extract.

The present disclosure is also directed to providing a pharmaceutical composition for preventing and treating stress diseases, which contains a *Platycodon grandiflorum* extract as an active ingredient.

The present disclosure is also directed to providing a pharmaceutical composition for preventing and treating stress diseases, which consists of a *Platycodon grandiflorum* extract.

The present disclosure is also directed to providing a pharmaceutical composition for preventing and treating stress diseases, which consists essentially of a *Platycodon grandiflorum* extract.

The present disclosure is also directed to providing a use of a *Platycodon grandiflorum* extract for preparing a therapeutic agent for stress diseases.

The present disclosure is also directed to providing a method for treating stress diseases, wherein an effective amount of a *Platycodon grandiflorum* extract is administered to an individual in need thereof.

Technical Solution

The present disclosure provides a food composition for preventing or alleviating stress diseases, which contains a *Platycodon grandiflorum* extract as an active ingredient.

The present disclosure also provides a food composition for preventing or alleviating stress diseases, which consists of a *Platycodon grandiflorum* extract.

The present disclosure also provides a food composition for preventing or alleviating stress diseases, which consists essentially of a *Platycodon grandiflorum* extract.

The present disclosure also provides a pharmaceutical composition for preventing and treating stress diseases, which contains a *Platycodon grandiflorum* extract as an active ingredient.

The present disclosure also provides a pharmaceutical composition for preventing and treating stress diseases, which consists of a *Platycodon grandiflorum* extract.

The present disclosure also provides a pharmaceutical composition for preventing and treating stress diseases, which consists essentially of a *Platycodon grandiflorum* extract.

The present disclosure also provides a use of a *Platycodon grandiflorum* extract for preparing a therapeutic agent for stress diseases.

The present disclosure also provides a method for treating stress diseases wherein an effective amount of a *Platycodon grandiflorum* extract is administered to an individual in need thereof.

Hereinafter, the present disclosure is described in detail.

The present disclosure provides a food composition for preventing or alleviating stress diseases, which contains a *Platycodon grandiflorum* extract as an active ingredient.

The present disclosure also provides a food composition for preventing or alleviating stress diseases, which consists of a *Platycodon grandiflorum* extract.

The present disclosure also provides a food composition for preventing or alleviating stress diseases, which consists essentially of a *Platycodon grandiflorum* extract.

The '*Platycodon grandiflorum*' of the present disclosure refers to a dried root of the perennial balloon flower. It has a neutral thermal nature and tastes bitter and pungent. The *Platycodon grandiflorum* has influence on the lungs and treats cough, phlegm and difficulty in breathing. It is effective in clearing the lungs, relieving tight chest, relieving coldness of the stomach, stopping cough and removing phlegm. It has been used from old times for anti-inflammatory activity, particularly for sore throat. It is used for throat pain, cough, phlegm, nasal congestion, asthma, bronchial trouble, pleurisy, headache, chill, tonsillitis, etc.

The 'stress' of the present disclosure refers to the psychological or physical tension experienced under an environmental condition which is difficult to adapt to. Continued stress may cause physical illness such as heart disease, gastric ulcer and hypertension, and may cause psychological maladjustment such as insomnia, anxiety and depression. The 'stress disease' refers to a stress-induced disease of a pathological mental condition affecting human's thought, emotion and behavior. It may include fatigue, headache, muscular pain, gastroenteric disorder, chest pain, abdominal pain, nervousness, sleep disorder, depression, anxiety, panic disorder, memory decline, etc. Specifically, it may be depression, anxiety or fatigue.

In an example of the present disclosure, restraint stress was applied by placing a mouse in a tube that that has holes for ventilation to induce depression, anxiety or fatigue.

The 'depression (depressive disorder)' of the present disclosure refers to a disease with decreased desire and depressed mood as main symptoms, which results in problems with daily activities through various cognitive, mental and physical symptoms. It is a severe disease affecting a person's life by causing change in emotion, thoughts, physical conditions, behavior, etc.

The 'anxiety' of the present disclosure, also known as anxiety disorder, includes diseases characterized by extreme fear, anxiety and related behavioral disorders. Anxiety is a feeling of uneasiness and worry involving the expectation to future threat, whereas fear is an emotional response to a real or perceived immediate threat. Anxiety and fear beyond normal levels may result in physical symptoms such as headache, increased heartbeats, increased respiratory rate, gastrointestinal trouble, etc., and difficulty in carrying out daily activities due to these problems may be diagnosed as anxiety disorder. Panic disorder, specific phobia, social phobia, obsessive-compulsive disorder, generalized anxiety disorder, acute stress disorder, posttraumatic stress disorder, etc. correspond to anxiety disorder.

The 'fatigue' of the present disclosure refers to a feeling of depleted energy due to tiredness and exhaustion. In general, it is an abnormal condition of lack of energy due to inability to recover from daily activities. It may be a normal phenomenon following intense activities. However, considerable fatigue felt after mild activities or even after enough rest may be considered a pathological symptom. The intensity of fatigue varies significantly from mild symptoms to total exhaustion. Although it is usually recovered after enough rest, chronic fatigue syndrome may be suspected if the fatigue is continued without special reason. It may be treated with drugs such as antidepressants, adrenocortical hormones, etc.

The present disclosure also provides a food composition for preventing or alleviating stress diseases, which further contains a *Citrus aurantium* extract.

The '*Citrus aurantium*' of the present disclosure has a cool nature. It tastes bitter, sour and acrid and is nontoxic. It relieves cough, dispels phlegm in the chest, communicates the small and large intestines well, and improves abdominal dropsy. It alleviates phlegm, expels evil qi, and heals itching, numbness, intestinal wind and hemorrhoids.

For example, as an extraction solvent of the extract of the present disclosure, one or more solvent selected from a group consisting of water, a $C_1$-$C_6$ alcohol such as ethanol, methanol, propanol, isopropanol and butanol and an organic solvent such as acetone, ether, chloroform, ethyl acetate, methylene chloride, hexane, cyclohexane, petroleum ether, diethyl ether and benzene may be used. Specifically, the extract of the present disclosure may be extracted using one or more solvent selected from a group consisting of water, ethanol, chloroform, ethyl acetate and 1-butanol. Most specifically, it may be extracted using water as a solvent.

The present disclosure provides a pharmaceutical composition for preventing or treating stress diseases, wherein a weight ratio of the *Platycodon grandiflorum* and the *Citrus aurantium* is (1-10):(1-10). Specifically, the mixing ratio of the *Platycodon grandiflorum* extract and the *Citrus aurantium* extract may be, for example, (1-10):1, (1-10):2, (1-10):3. (1-10):4. (1-10):5. (1-10):6, (1-10):7. (1-10):8. (1-10):9. (1-10):10, 1:(1-10), 2:(1-10), 3:(1-10), 4:(1-10), 5:(1-10), 6:(1-10), 7:(1-10). 8:(1-10), 9:(1-10) or 10:(1-10) based on weight, more specifically 1:1, 1:2, 1:3, 1:4, 1:5, 1:6, 1:7, 1:8, 1:9, 1:10, 2:1, 2:2, 2:3, 2:4, 2:5, 2:6, 2:7, 2:8, 2:9, 2:10, 3:1, 3:2, 3:3. 3:4, 3:5, 3:6, 3:7, 3:8, 3:9, 3:10, 4:1, 4:2, 4:3, 4:4, 4:5, 4:6, 4:7, 4:8, 4:9. 4:10, 5:1, 5:2, 5:3, 5:4, 5:5, 5:6, 5:7, 5:8, 5:9, 5:10, 6:1, 6:2, 6:3, 6:4, 6:5, 6:6, 6:7, 6:8, 6:9, 6:10, 7:1, 7:2, 7:3, 7:4, 7:5, 7:6, 7:7, 7:8, 7:9, 7:10, 8:1, 8:2, 8:3, 8:4, 8:5, 8:6, 8:7, 8:8, 8:9, 8:10, 9:1, 9:2, 9:3, 9:4, 9:5, 9:6, 9:7, 9:8, 9:9, 9:10, 10:1, 10:2, 10:3, 10:4, 10:5, 10:6, 10:7, 10:8, 10:9 or 10:10 based on weight. However, the weight ratio is not limited as long as it is within a range of (1-10):(1-10). Most specifically, the weight ratio of the *Platycodon grandiflorum* and the *Citrus aurantium* extract may be 1:1.

In an example of the present disclosure, 150 mg/kg of the *Platycodon grandiflorum* and 150 mg/kg of the *Citrus aurantium* may be mixed to prepare a mixture with a concentration of 300 mg/kg.

The food composition using the *Platycodon grandiflorum* extract or a mixture of the *Platycodon grandiflorum* extract and the *Citrus aurantium* extract according to the present disclosure includes all formulations such as functional food, nutritional supplement, health food, food additive, etc. These formulations may be prepared into various forms according to common methods known in the art. The food composition may be prepared into a drink, a granule or a powder. In addition, the food composition of the present disclosure may be mixed with any substance or active ingredient known to have hair growth-promoting and anti-inflammatory effects.

For example, as a health food, the food composition of the present disclosure itself may be prepared into a tea, a juice, a drink, a granule, a capsule or a powder. In addition, the food composition of the present disclosure may be mixed with a substance or active ingredient known to be effective in reducing body fat, improving cholesterol or lowering blood pressure.

The functional food may be prepared by adding the food composition of the present disclosure to a beverage (including an alcoholic beverage), fruit and processed foods thereof (e.g., canned fruit, bottled fruit, jam, marmalade, etc.), fish, meat and processed foods thereof (e.g., ham, sausage, corned beef, etc.), bread and noodles (e.g., udon, buckwheat noodles, ramen, spaghetti, macaroni, etc.), fruit juice and drinks, cookie, taffy, dairy products (e.g., butter, cheese, etc.), edible vegetable oil, margarine, vegetable protein, retort pouch, frozen food, seasoning (e.g., soybean paste, soya, sauce, etc.), etc.

Specifically, the content of the food composition according to the present disclosure in the finally prepared food may be 0.01-50 wt %, although not being limited thereto. The food composition of the present disclosure may be prepared into a powder or a concentrate to be used as a food additive.

The present disclosure also provides a pharmaceutical composition for preventing and treating stress diseases, which contains a *Platycodon grandiflorum* extract as an active ingredient.

The present disclosure also provides a pharmaceutical composition for preventing and treating stress diseases, which consists of a *Platycodon grandiflorum* extract.

The present disclosure also provides a pharmaceutical composition for preventing and treating stress diseases, which consists essentially of a *Platycodon grandiflorum* extract.

The present disclosure also provides a pharmaceutical composition for preventing and treating stress diseases, which further contains a *Citrus aurantium* extract.

The pharmaceutical composition according to the present disclosure may contain the *Platycodon grandiflorum* extract or a mixture of the *Platycodon grandiflorum* extract and the *Citrus aurantium* extract alone, or may be formulated into an appropriate form together with a pharmaceutically acceptable carrier and may further contain an excipient or a diluent. The term 'pharmaceutically acceptable' means that the substance is physiologically acceptable and is nontoxic without causing allergic or other similar adverse reactions when administered to a human.

For example, the pharmaceutically acceptable carrier may include a carrier for oral administration or a carrier for parenteral administration. The carrier for oral administration may include lactose, starch, a cellulose derivative, magnesium stearate, stearic acid, etc. In addition, it may include various drug delivery systems used for oral administration of peptide drugs. And, the carrier for parenteral administration may include water, suitable oil, saline, aqueous glucose, glycol, etc., and may further include a stabilizer and a preservative. As a suitable stabilizer, there is an antioxidant such as sodium hydrogen sulfite, sodium sulfite or ascorbic acid. As a suitable preservative, there are benzalkonium chloride, methyl- or propylparaben and chlorobutanol. The pharmaceutical composition of the present disclosure may further contain a lubricant, a wetting agent, a sweetener, a flavorant, an emulsifier, a suspending agent, etc. in addition to the above-described ingredients. Other pharmaceutically acceptable carriers and agents are described in the following literature (Remington's Pharmaceutical Sciences, 19th ed., Mack Publishing Company, Easton, Pa., 1995).

The composition of the present disclosure may be administered to a mammal including human by any method. For example, it may be administered orally or parenterally. The parenteral administration method may be, but is not limited to, intravenous, intramuscular, intraarterial, intramedullar, intrathecal, intracardiac, transcutaneous, subcutaneous, intraperitoneal, intranasal, enteral, topical, sublingual or rectal administration.

The pharmaceutical composition of the present disclosure may be formulated into preparations for oral or parenteral administration according to the administration routes described above.

For the preparations for oral administration, the composition of the present disclosure may be formulated in the form of a powder, a granule, a tablet, a pill, a sugar-coated tablet, a capsule, a liquid, a gel, a syrup, a slurry or a suspension using a method known in the art. For example, the preparations for oral administration may be prepared as a tablet or a sugar-coated tablet by mixing the active ingredient with a solid excipient, grinding the resulting mixture, adding a suitable additive, and then processing it into a granular mixture. Examples of a suitable excipient may include a saccharide including lactose, dextrose, sucrose, sorbitol, mannitol, xylitol, erythritol and maltitol, a starch including corn starch, wheat starch, rice starch and potato starch, a cellulose including cellulose, methyl cellulose, sodium carboxymethyl cellulose and hydroxypropylmethyl cellulose, and a filler such as gelatin and polyvinylpyrrolidone. In addition, a disintegrant such as crosslinked polyvinylpyrrolidone, agar, alginic acid or sodium alginate may be optionally added. Furthermore, the pharmaceutical composition of the present disclosure may further include an anti-aggregating agent, a lubricant, a wetting agent, a flavor, an emulsifier, a preservative, etc.

For the preparations for parenteral administration, the composition of the present disclosure may be formulated as an injection, a cream, a lotion, an ointment, an oil, an emulsion, a gel, an aerosol or a nasal inhalant according to a method known in the art. These formulations are disclosed in the following literature (Remington's Pharmaceutical Science, 19th ed., Mack Publishing Company, Easton, Pa., 1995), which is a formulary generally known in all fields of pharmaceutical chemistry.

The total effective amount of the composition of the present disclosure may be administered to a subject as a single dose or as multiple doses according to a fractionated treatment protocol. The pharmaceutical composition of the present disclosure may contain various contents of the active ingredient according to the severity of a disease. A daily dose of the pharmaceutical composition of the present disclosure may be specifically approximately 0.01 μg to 10,000 mg, more specifically 0.1 μg to 500 mg, most preferably 100 mg to 500 mg, per kilogram of the body weight of a patient. However, the effective dose of the pharmaceutical composition for a patient is determined by considering various parameters such as the patient's age, body weight, health condition and sex, the severity of a disease, diet and excretion ratio, as well as a formulation method, an administration route and a treatment cycle. In consideration of these parameters, a suitable effective dose of the composition of the present disclosure may be determined by those of ordinary skill in the art. There are no particular limits to a formulation, administration route and administration method of the pharmaceutical composition of the present disclosure as long as the composition exhibits the effects of the present disclosure.

In an example of the present disclosure, after orally administering each of an SOCG (So-o-chim-tang-gami-bang) extract and the extracts of the drugstuffs constituting SOCG, linderae radix, licorice, rhizoma cyperi, elecampane, *Platycodon grandiflorum* and *Citrus aurantium* to a mouse, restraint stress was applied 2 hours later. After inducing depression with the restraint stress for 14 days, forced swim test was conducted on day 15. As a result, it was confirmed that the groups treated with the extracts showed shorter immobility duration than the control group, and the groups treated with the *Platycodon grandiflorum* extract, the *Citrus aurantium* extract and the rhizoma cyperi extract showed shorter immobility duration than the group treated with the SOCG extract (see Example 1 and FIG. 1). Among them, because rhizoma cyperi has severe side effects for people with weak energy or people with dryness and heat, the rhizoma cyperi was excluded and only the *Platycodon grandiflorum* extract and the *Citrus aurantium* extract were used in the present disclosure.

In another example of the present disclosure, after orally administering an SOCG (So-o-chim-tang-gami-bang) extract, a *Citrus aurantium* extract or a *Platycodon grandiflorum* extract to a mouse or a rat, restraint stress was applied 2 hours later. After inducing depression with the restraint stress for 14 days, forced swim test was conducted on day 15. As a result, it was confirmed that the group treated with the SOCG extract, the *Citrus aurantium* extract or the *Platycodon grandiflorum* extract showed increased total global activity and shorter immobility duration. In addition, the group treated with the *Citrus aurantium* extract or the *Platycodon grandiflorum* extract showed more increase in total global activity and shorter immobility duration as compared to the group treated with the SOCG extract (see Example 2-1 and FIG. 2).

In another example of the present disclosure, after administering 300 mg/kg of a SOCG extract and a *Citrus aurantium* extract and a *Platycodon grandiflorum* extract at different concentrations of 150, 300 and 600 mg/kg to a mouse or a rat, depression was induced by applying restraint stress for 14 days and then forced swim test was conducted. As a result, it was confirmed that the groups treated with 300 and 600 mg/kg of the *Citrus aurantium* extract and the group treated with 300 mg/kg of the *Platycodon grandiflorum* extract showed the most active movement and the shortest immobility duration (see Example 2-2, FIG. 3a and FIG. 3b).

In another example of the present disclosure, after administering a mixture of a *Citrus aurantium* extract and a *Platycodon grandiflorum* extract or a SOCG mixture to a mouse or a rat, depression was induced by applying restraint stress days and then forced swim test was conducted. As a result, it was confirmed that the groups to which the SOCG and the mixture of *Platycodon grandiflorum* and *Citrus aurantium* were administered showed decreased in immobility duration, and the group to which the mixture of *Platycodon grandiflorum* and *Citrus aurantium* was administered showed shorter immobility duration than the group to which the SOCG was administered (see Example 3, FIG. 4 and FIG. 5).

In another example of the present disclosure, after administering a mixture of *Platycodon grandiflorum* and *Citrus aurantium* to a mouse and applying restraint stress, blood was taken and the concentration of the stress hormone corticosterone was measured by enzyme-linked immunosorbent assay. As a result, it was confirmed that a stress control group showed increase in corticosterone level, whereas the group to which the mixture of *Platycodon grandiflorum* and *Citrus aurantium* was administered showed decrease in corticosterone level (see Example 4-1 and FIG. 6).

In another example of the present disclosure, after administering amitryptyline, an SOCG mixture or a mixture of *Platycodon grandiflorum* and *Citrus aurantium* to a rat and inducing depression by applying restraint stress, blood was taken and the concentration of the stress hormone corticosterone was measured by enzyme-linked immunosorbent assay. As a result, it was confirmed that a stress control group showed increase in corticosterone level, whereas the group to which the SOCG mixture was administered and the group to which the mixture of *Platycodon grandiflorum* and *Citrus aurantium* was administered showed decrease in corticosterone level. The group to which the mixture of *Platycodon grandiflorum* and *Citrus aurantium* was administered showed a lower concentration as compared to the group to which the SOCG mixture was administered (see Example 4-2 and FIG. 7).

Figure 8:
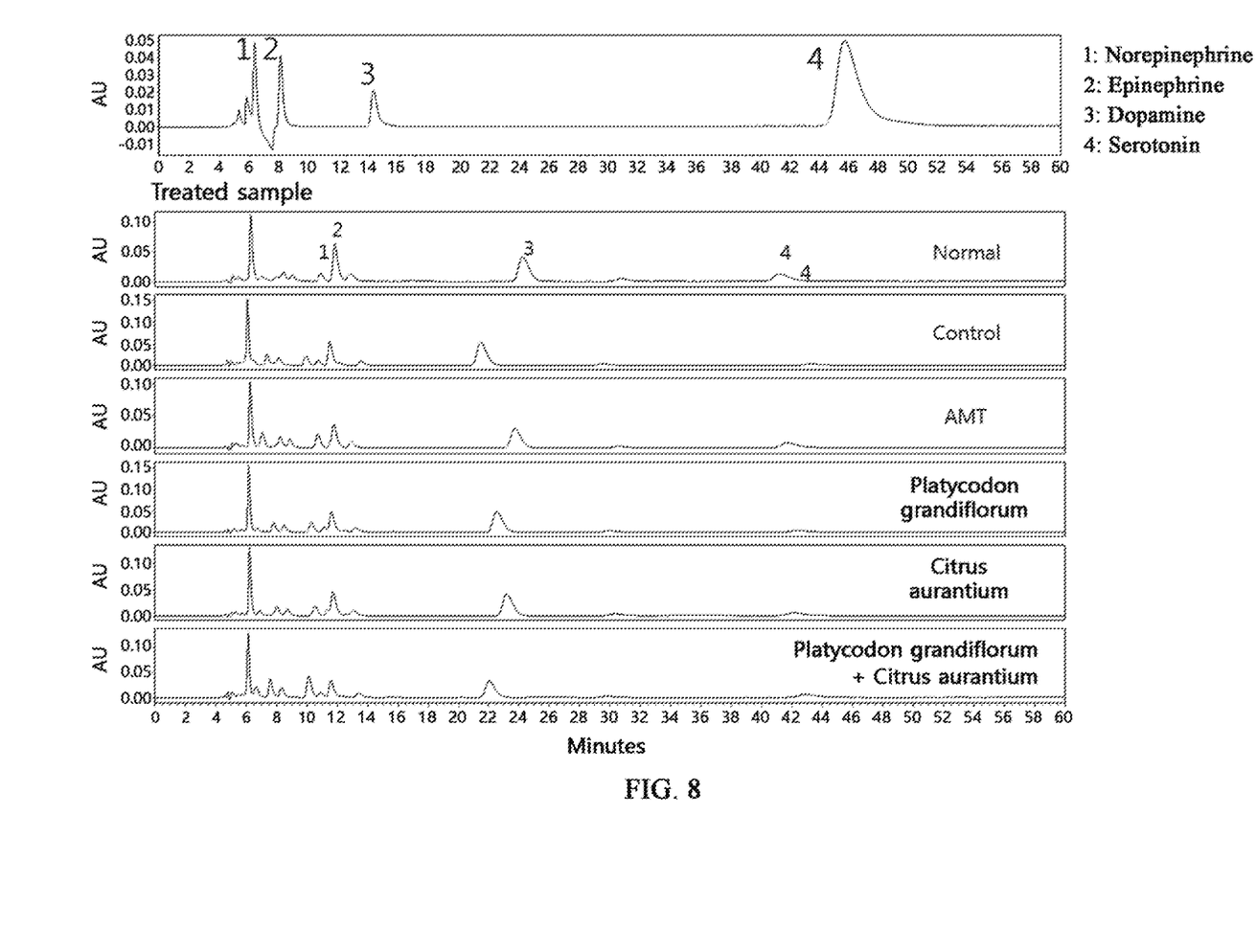
FIG. 8 shows a result of administering 200 mg/kg of a *Platycodon grandiflorum* extract, 200 mg/kg of a *Citrus aurantium* extract or 300 mg/kg of a mixture of *Platycodon grandiflorum* and *Citrus aurantium* to a mouse with restraint stress-induced depression and measuring the concentration of neurotransmitters in a brain tissue by HPLC.

In another example of the present disclosure, after administering a *Platycodon grandiflorum* extract, a *Citrus aurantium* extract and a mixture of *Platycodon grandiflorum* and *Citrus aurantium* to a mouse and applying restraint stress, the brain tissue was extracted and the level of the neurotransmitters, norepinephrine, epinephrine, dopamine and serotonin, in the hippocampal region and the cerebral region was measured by HPLC. As a result, it was confirmed that the *Platycodon grandiflorum* extract, the *Citrus aurantium* extract, and the mixture of *Platycodon grandiflorum* and *Citrus aurantium* are effective in inhibiting the decrease of neurotransmitters in the brain of the mouse with stress-induced depression (see Example 5 and FIGS. 8-10).

In another example of the present disclosure, after administering a mixture of *Platycodon grandiflorum* and *Citrus aurantium* to a mouse and inducing depression by applying restraint stress, DNA was extracted and the genes significantly expressed in the group to which the mixture of *Platycodon grandiflorum* and *Citrus aurantium* was administered were screened by comparing the expression level of genes affecting recovery from fatigue by a microarray method. Then, the signaling pathway affecting recovery from fatigue was investigated using the same. It was confirmed that the mixture of *Platycodon grandiflorum* and *Citrus aurantium* improves stress-induced fatigue by promoting the expression of the genes related with recovery from fatigue (see Example 6).

The present disclosure also provides a use of a *Platycodon grandiflorum* extract for preparing a therapeutic agent for stress diseases.

The agent may further contain a *Citrus aurantium* extract.

The present disclosure also provides a method for treating stress diseases wherein an effective amount of a *Platycodon grandiflorum* extract is administered to an individual in need thereof.

The present disclosure also provides a method for treating stress diseases wherein a *Citrus aurantium* extract is further administered.

In the present disclosure, the 'effective amount' refers to an amount capable of exhibiting an effect of alleviating, treating, preventing, detecting, diagnosing, suppressing or reducing stress diseases when administered to an individual. The 'individual' may be an animal, specifically a mammal, particularly human, or a cell, a tissue, an organ, etc. derived from an animal. The individual may be a patient in need of the above-described effect.

In the present disclosure, the 'treatment' comprehensively refers to alleviation of stress diseases or symptoms of the stress diseases. It may include treatment or substantial prevention of the diseases or alleviation of conditions. It may include alleviation, treatment or prevention of at least one or most symptoms of the stress diseases, although not being limited thereto.

In the present disclosure, the term 'comprising' is used synonymously with 'containing' or 'characterized by' and does not exclude the presence of additional constituent elements, steps, etc. with regard to a composition or a method. The term 'consisting of' excludes the presence of additional constituent elements, steps, etc. unless stated otherwise. The term 'consisting essentially of' means, with regard to a composition or a method, means that, in addition to the mentioned constituent elements or steps, other constituent elements, steps, etc. which do not substantially affect basic characteristics are included.

Advantageous Effects

The present disclosure provides a composition for preventing, alleviating or treating stress diseases, which contains a *Platycodon grandiflorum* extract or a mixture of a *Platycodon grandiflorum* extract and a *Citrus aurantium* extract as an active ingredient. The present disclosure can be usefully utilized in preparation of a therapeutic agent for depression and anxiety, which are stress diseases, with few side effects using a natural product, and a health functional food effective in alleviation of depression and anxiety, which are stress diseases, and fatigue.

BEST MODE

Hereinafter, the present disclosure is described in detail.

However, the following examples merely illustrate the present disclosure and the contents of the present disclosure are not limited by the examples.

<Experimental Methods>

Preparation of Mixture of *Platycodon Grandiflorum* and *Citrus Aurantium*

Each of *Platycodon grandiflorum* (platycodi radix) and *Citrus aurantium* was added to water of 10 times based on weight and hot-water extracted at 90-100° C. for 3 hours. After filtering the extraction solvent using a filter paper, a *Citrus aurantium* extract and a *Platycodon grandiflorum* extract were prepared by conducting concentration under reduced pressure using a rotary evaporator at 60° C. or below. Then, a mixture of *Platycodon grandiflorum* and *Citrus aurantium* was prepared by mixing 150 mg/kg of the *Platycodon grandiflorum* extract and 150 mg/kg of the *Citrus aurantium* extract at a weight ratio of 1:1.

Administration of *Platycodon Grandiflorum* Extract, *Citrus Aurantium* Extract or Mixture of *Platycodon Grandiflorum* and *Citrus Aurantium*

The sample was administered orally 2 hours before applying restraint stress. Physiological saline was administered orally to a normal group (na) and a stress control group (control). 300 mg/kg of an SOCG (So-o-chim-tang-gami-bang) extract was administered to an SOCG group. 150, 300 or 600 mg/kg of the *Citrus aurantium* extract was administered to *Citrus aurantium* groups. 150, 300 or 600 mg/kg of the *Platycodon grandiflorum* extract was administered to *Platycodon grandiflorum* groups. In addition, 150 mg/kg of the *Platycodon grandiflorum* extract and 150 mg/kg of the *Citrus aurantium* extract were mixed to prepare a 300 mg/kg mixture. The sample administration volume was 0.1 mL for a mouse and 0.3 mL for WKY.

Stress-Induced Depression Model

C57/BL6 mice (male, 7-week-old) were purchased from Dae Han Bio Link (Korea) and Wistar-Kyoto rats (WKY) were acquired from Kyungpook National University. The mice and WKY were reared in different cages. They were used for experiments after accustoming to the laboratory environment of temperature 22±2° C., humidity 50-70%, and lighting for 12 hours (08:00-20:00) with illuminance of 150-300 Lux for a week while providing solid feed (Samyang Feed) and water sufficiently.

Restraint stress was applied to induce depression. The C57BL/6 mouse accustomed to the laboratory environment for a week was individually placed in a 50-mL Falcon tube with holes for ventilation. For the WKY, a restraint stress device for rats was used. The animal was restrained for 14 days, 6 hours a day, to induce depression.

Forced Swim Test (FST)

After filling a transparent acrylic cylindrical water bath (Vision Scientific Co., Korea) with water at room temperature, the depression-induced mouse or WKY was forced to swim for 15 minutes. 24 hours later, the duration of immobility was measured while forcing the animal to swim for 6 minutes under the same condition. The measurement was made for the last 4 minutes and recording was made conducted with a video camera. The total global activity of the animal in water was analyzed with a video-tracking software (SMART 3.0, Panlab, Spain).

Enzyme-Linked Immunosorbent Assay

Serum was obtained by centrifuging (Labogene, Gyrozen, Daejeon, Korea) blood extracted from the depression-induced mouse or rat. A corticosterone ELISA kit (Enzo Life Science, Cat. ADI-900-097) was used for enzyme-linked immunosorbent assay. After adding 100 μL of the mouse or rat serum and standard to a pre-coated 96-well plate included in the kit, 50 μL of the blue conjugate reagent was added to each well containing the serum and standard. After adding 50 μL of a capture antibody to the well containing the serum and standard, incubation was performed on a shaker at room temperature and 500 rpm for 2 hours. After draining the well and washing 3 times with a wash solution, 200 μL of the pNpp substrate solution was added to all wells and incubation was performed at room temperature for 1 hour. Then, after treating with 50 μL of a stop solution, absorbance was measured at 405 nm using a microspectrophotometer (Molecular Device, Sunnyvale, Calif., USA).

Preparation of Sample for Specific Brain Regions

According to a method specified for the hippocampal and cortical region of the brain (Adams, 2013), the brain tissue was homogenized by adding a phosphate buffer of about 2 times of weight. 100 μL of the homogenate was immediately added to 300 μL of cold perchloric acid (0.1 M in PBS), and the mixture was completely homogenized by sonicating for 1 minute. Then, after keeping the homogenate on ice for 10 minutes, centrifugation was performed at 4° C. and 12000 rpm for 15 minutes. Subsequently, the supernatant was filtered through a 0.2-μm syringe filter and then subjected to HPLC (high-performance liquid chromatography) analysis.

Chromatographic Analysis

Neurotransmitters were analyzed using a liquid chromatographic water system (Waters Corp., Milford, Mass., USA) coupled with a photodiode array detector and a separation module (e2695) according to a specified method (Church 2005). For the analysis of neurotransmitters, a mixture of 1% citric acid, 2% $K_2HPO_4$, 1 mM EDTA, 7 mg/mL sodium octyl sulfate and 1.2% methanol and a C18 column (250 mm, 4.6 mm, 5 μm) were used. 20 μL of an isocratic mobile phase was injected at a flow rate of 0.5 mL/min at a wavelength of 254 nm. Epinephrine, norepinephrine, dopamine and serotonin were used as standards at a concentration of 1 mg/mL.

Statistical Analysis

All data were represented as mean±standard error (SEM). The result for each test group was statistically analyzed using a statistical program (one-way ANOVA; post-hoc Tukey test), and significance was tested at a level of P<0.05 (*P<0.05, P<0.01, *P<0.001).

EXAMPLE 1

Effect of Extracts of Drugstuffs Constituting SOCG on Depression

Experiment was conducted as follows in order to investigate the effect of each of the drugstuffs constituting SOCG (So-o-chim-tang-gami-bang), linderae radix, licorice, rhizoma cyperi, elecampane, *Platycodon grandiflorum* and *Citrus aurantium*, on depression.

After orally administering physiological saline to C57/BL6 mice (male, 7-week-old) of a normal group and a stress control group, 300 mg/kg of each of an SOCG extract, a linderae radix extract, a licorice extract, a rhizoma cyperi extract, an elecampane extract, a *Platycodon grandiflorum* extract and a *Citrus aurantium* extract was administered. Restraint stress was applied 2 hours later. After applying the restraint stress for 14 days, 6 hours a day, forced swim test was conducted on day 15.

Figure 1:
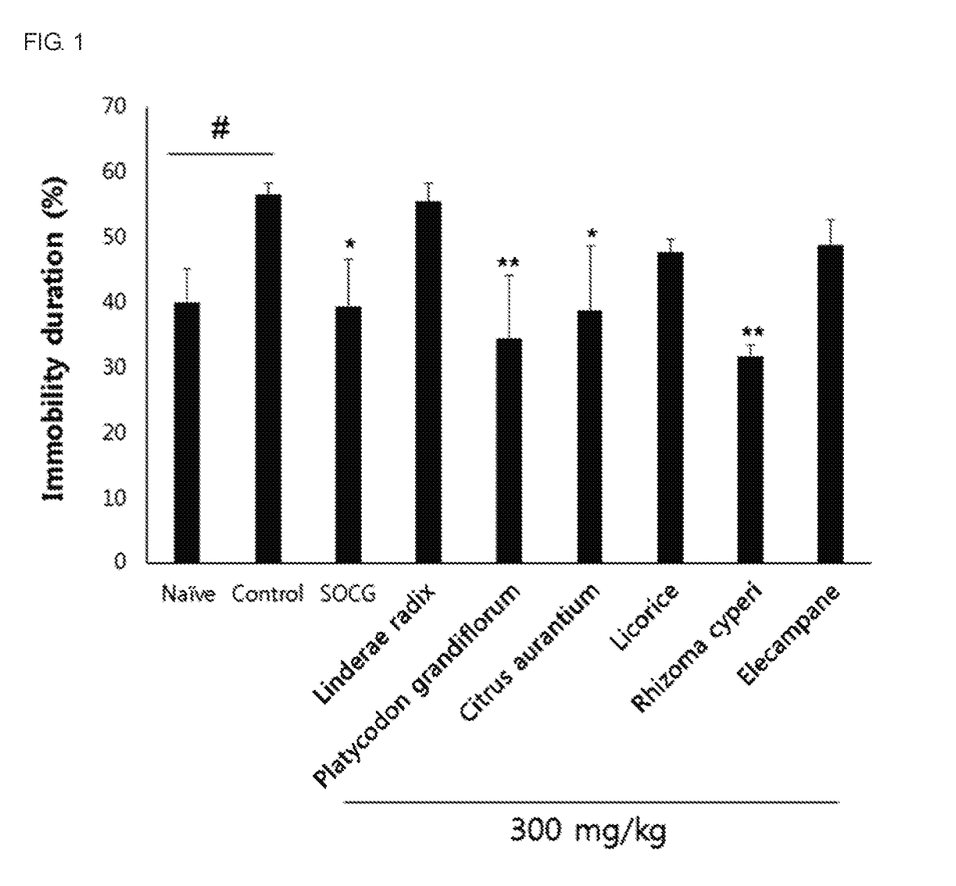
FIG. 1 shows a result of administering 300 mg/kg of SOCG (So-o-chim-tang-gami-bang), linderae radix, licorice, rhizoma cyperi, elecampane, *Platycodon grandiflorum* and *Citrus aurantium* extracts to a mouse, inducing depression by applying restraint stress, and then conducting forced swim test (#P<0.05 vs. na, ***P<0.001 vs. Control).

As seen from FIG. 1, it was confirmed that immobility duration was decreased in the group treated with each extract as compared to the stress control group, and the groups treated with the *Platycodon grandiflorum* extract, the *Citrus aurantium* extract and the rhizoma cyperi extract showed shorter immobility duration than the group treated with the SOCG extract.

EXAMPLE 2

Effect of *Platycodon Grandiflorum* Extract and *Citrus Aurantium* Extract on Depression <2-1> Effect of *Platycodon Grandiflorum* Extract and *Citrus Aurantium* Extract on Depression Experiment was conducted as follows in order to investigate the effect of the *Platycodon grandiflorum* extract and the *Citrus aurantium* extract alone on depression.

Physiological saline was orally administered to C57/BL6 mice (male, 7-week-old) of a normal group and a stress control group, 300 mg/kg of the SOCG extract was administered to an SOCG group, and 200 mg/kg of each of the *Platycodon grandiflorum* extract and the *Citrus aurantium* extract was administered. Restraint stress was applied 2 hours later. After applying the restraint stress for 14 days, 6 hours a day, forced swim test was conducted on day 15.

Figure 2:
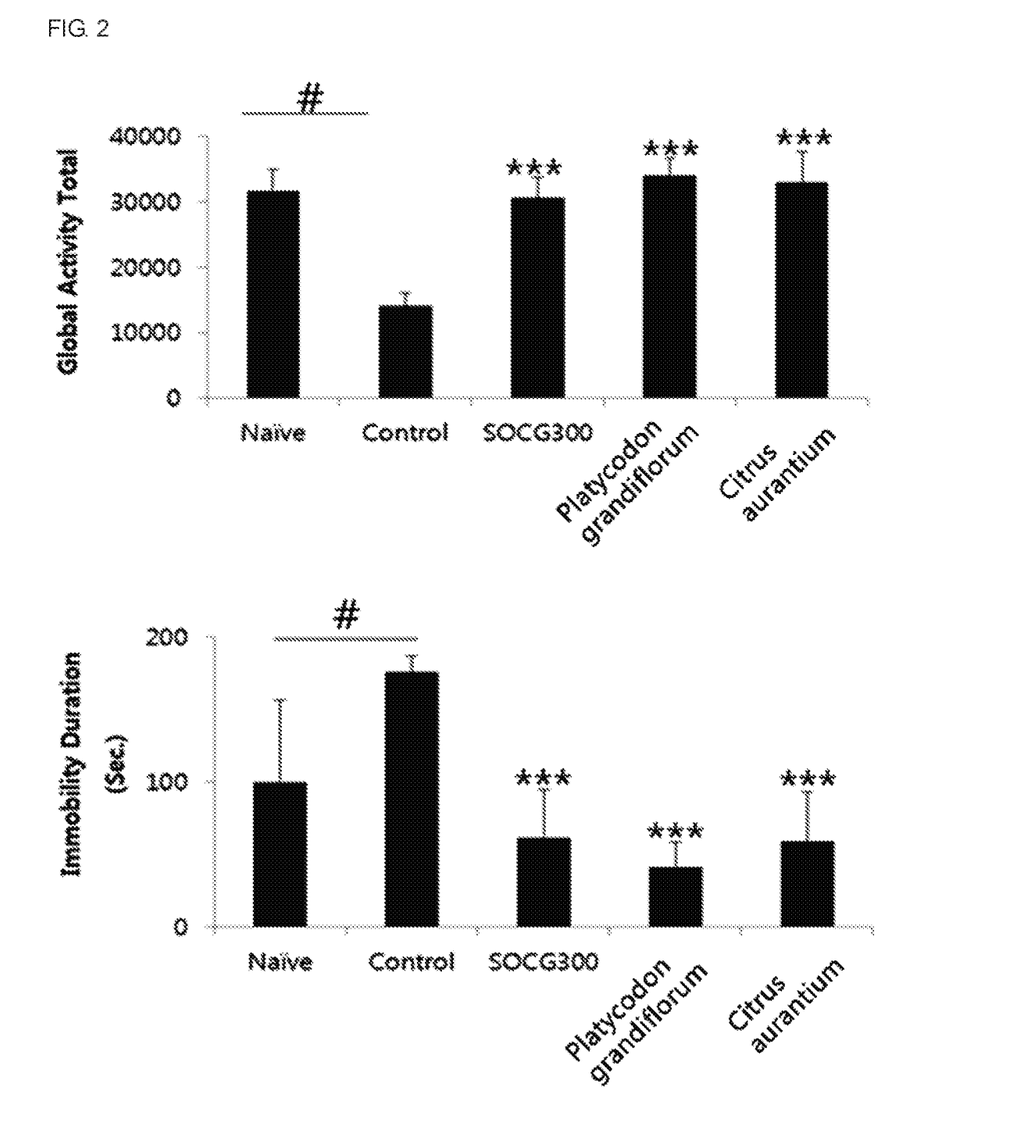
FIG. 2 shows a result of administering 300 mg/kg of an SOCG (So-o-chim-tang-gami-bang) extract and 200 mg/kg of *Platycodon grandiflorum* and *Citrus aurantium* extracts from among the drugstuffs constituting SOCG to a mouse with restraint stress-induced depression for 14 days and conducting forced swim test on day 15 (#P<0.05 vs. na, ***P<0.001 vs. Control).

As seen from FIG. 2, total global activity was increased and immobility duration was decreased as compared to the stress control group. In addition, it was confirmed that the group treated with the *Platycodon grandiflorum* extract or the *Citrus aurantium* extract alone showed increased total global activity and decreased immobility duration as compared to the group treated with the SOCG extract.

Through this, it was confirmed that the *Platycodon grandiflorum* extract and the *Citrus aurantium* extract are effective in alleviating depression.

<2-2> Effect of *Platycodon Grandiflorum* Extract and *Citrus Aurantium* Extract on Depression Depending on Concentration Experiment was conducted as follows in order to investigate the effect of the *Platycodon grandiflorum* extract and the *Citrus aurantium* extract depending on concentration.

Physiological saline was orally administered to C57/BL6 mice (male, 7-week-old) of a normal group and a stress control group, 300 mg/kg of the SOCG extract was administered to an SOCG group, and 150, 300 or 600 mg/kg of each of the *Platycodon grandiflorum* extract and the *Citrus aurantium* extract was administered. Restraint stress was applied 2 hours later. After applying the restraint stress for 14 days, 6 hours a day, forced swim test was conducted on day 15.

Figure 3A:
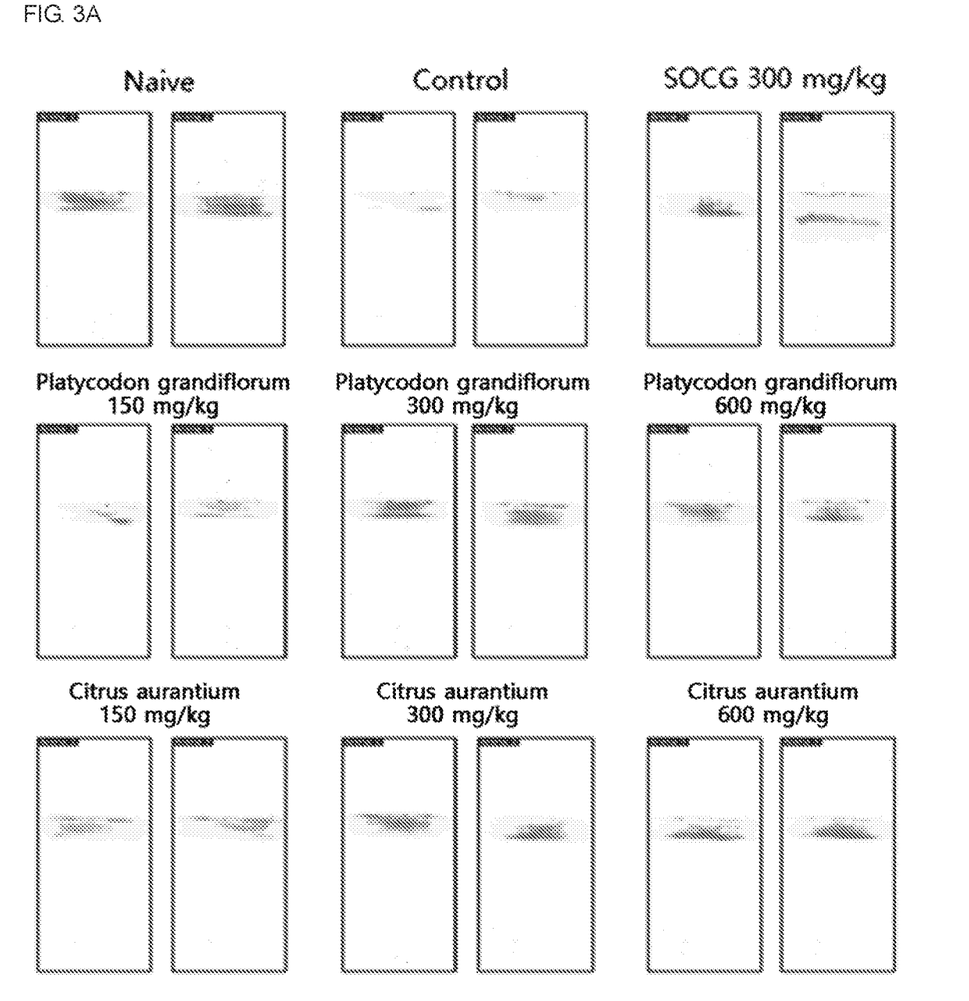
FIG. 3a and FIG. 3b show total global activity (FIG. 3a) and immobility duration (FIG. 3b) as a result of administering 300 mg/kg of an SOCG extract and 150 mg/kg, 300 mg/kg or 600 mg/kg of a *Platycodon grandiflorum* or *Citrus aurantium* extract to a mouse with restraint stress-induced depression for 14 days and conducting forced swim test on day 15.
Figure 3B:
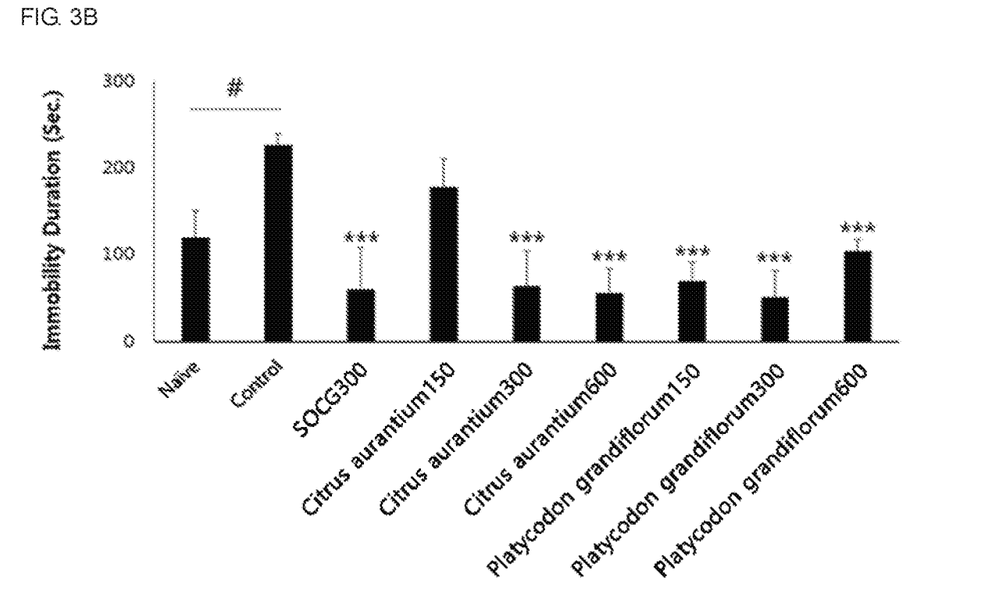

As seen from FIG. 3*a* and FIG. 3*b*, the group treated with 300 mg/kg of the *Citrus aurantium* extract and the group treated with 300 mg/kg of the *Platycodon grandiflorum* extract showed the most active movement (FIG. 3*a*). In addition, the group treated with 300 or 600 mg/kg of the *Citrus aurantium* extract showed the shortest immobility duration, and the group treated with 300 mg/kg of the *Platycodon grandiflorum* showed the shortest immobility duration.

Through this, it was confirmed that administration of 300 mg/kg of the *Platycodon grandiflorum* extract or the *Citrus aurantium* extract has the largest effect of alleviating depression.

EXAMPLE 3

Effect of Mixture of *Platycodon Grandiflorum* and *Citrus Aurantium* on Depression Experiment was conducted as follows in order to investigate the effect of a mixture of *Platycodon grandiflorum* and *Citrus aurantium* on depression.

<3-1> Effect of Mixture of *Platycodon Grandiflorum* and *Citrus Aurantium* on Depression-Induced Mouse 300 mg/kg of a mixture of *Platycodon grandiflorum* and *Citrus aurantium* was prepared by mixing 150 mg/kg of a *Platycodon grandiflorum* extract and 150 mg/kg of a *Citrus aurantium* extract. Physiological saline was orally administered to C57/BL6 mice (male, 7-week-old) of a normal group and a stress control group, 30 mg/kg of amitriptyline (A8404-10G, Sigma-Aldrich, USA) was administered to a positive control group, 300 mg/kg of the SOCG extract was administered to an SOCG group, and 300 mg/kg of the mixture of *Platycodon grandiflorum* and *Citrus aurantium* was administered. Restraint stress was applied 2 hours later. After applying the restraint stress for 14 days, 6 hours a day, forced swim test was conducted on day 15.

Figure 4:
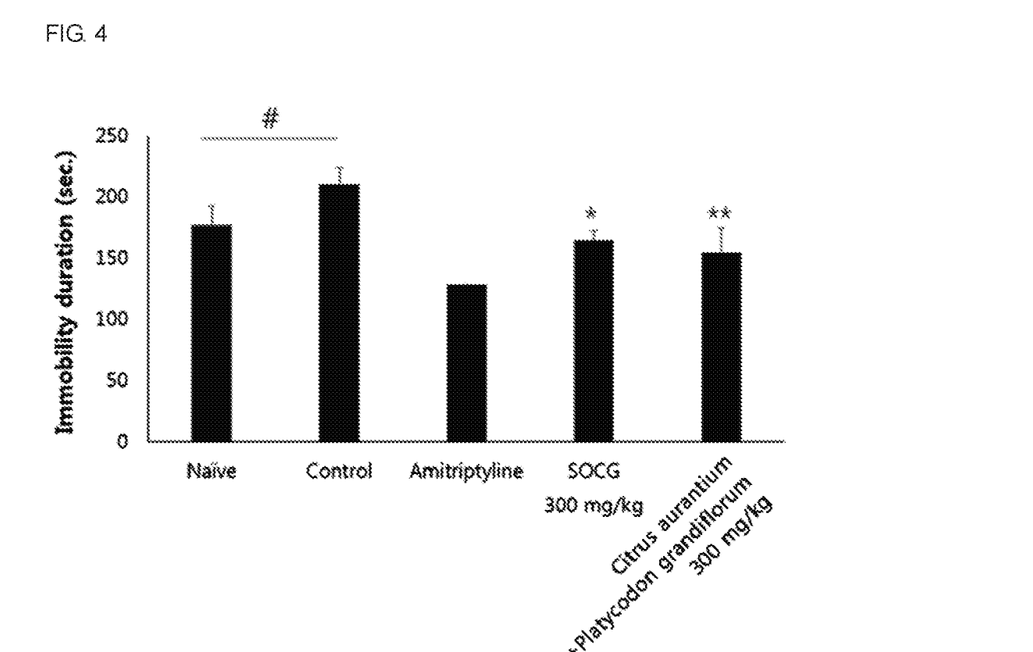
FIG. 4 shows a result of administering 30 mg/kg of amitriptyline, 300 mg/kg of SOCG or 300 mg/kg of a mixture of *Platycodon grandiflorum* and *Citrus aurantium* extracts at a weight ratio of 1:1 to a mouse with restraint stress-induced depression for 14 days and conducting forced swim test (#P<0.05 vs. na, *P<0.05, **P<0.01 vs. Control).

As seen from FIG. 4, it was confirmed that immobility duration was decreased in the group to which SOCG was administered and the group to which the mixture of *Platycodon grandiflorum* and *Citrus aurantium* was administered, and the group to which the mixture of *Platycodon grandiflorum* and *Citrus aurantium* was administered showed shorter immobility duration than the group to which SOCG was administered.

<3-2> Effect of Mixture of *Platycodon Grandiflorum* and *Citrus Aurantium* on Depression-Induced Rat Physiological saline was orally administered to depression-induced Wistar-Kyoto rats (WKY) of a normal group and a stress control group, 10 mg/kg of amitriptyline (A8404-10G, Sigma-Aldrich) was administered to a positive control group, 300 mg/kg of the SOCG extract was administered to an SOCG group, and 300 mg/kg of the mixture of *Platycodon grandiflorum* and *Citrus aurantium* was administered. Restraint stress was applied 2 hours later. After applying the restraint stress for 14 days, 6 hours a day, forced swim test was conducted on day 15.

Figure 5:
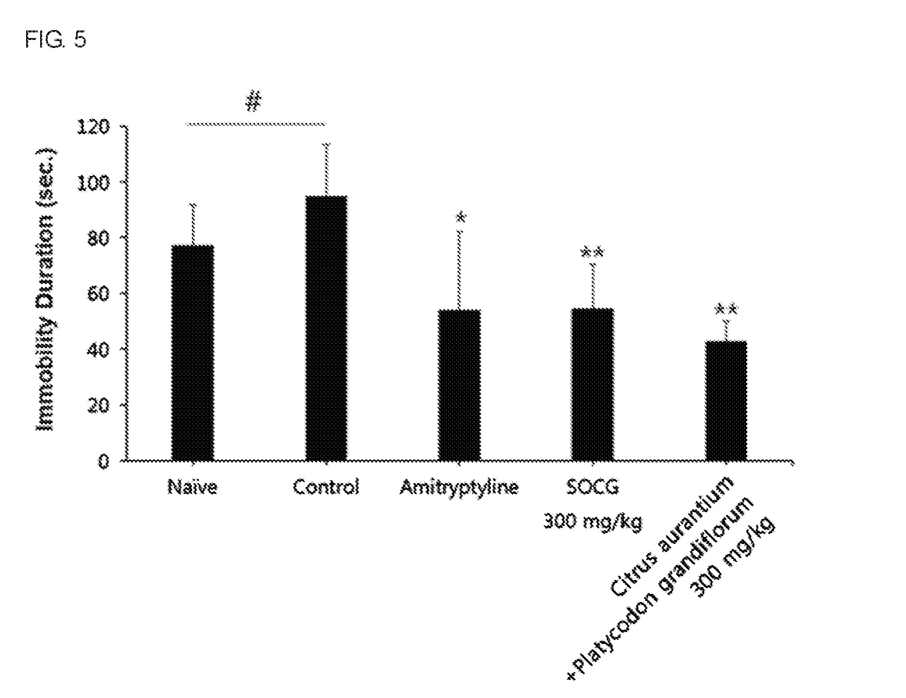
FIG. 5 shows a result of administering 10 mg/kg of amitriptyline, 300 mg/kg of SOCG or 300 mg/kg of a mixture of *Platycodon grandiflorum* and *Citrus aurantium* to a Wistar-Kyoto rat (WKY) with restraint stress-induced depression for 14 days and conducting forced swim test on day 15 (#P<0.05 vs. na, *P<0.05, **P<0.01 vs. Control).

As seen from FIG. 5, it was confirmed that the group to which the SOCG mixture was administered and the group to which the mixture of *Platycodon grandiflorum* and *Citrus aurantium* was administered showed shorter immobility duration as compared to the control group, and the group to which the mixture of *Platycodon grandiflorum* and *Citrus aurantium* was administered showed the shortest immobility duration.

Through this, it was confirmed that the mixture of *Platycodon grandiflorum* and *Citrus aurantium* is more effective in alleviating depression than the SOCG mixture.

EXAMPLE 4

Effect of Mixture of *Platycodon Grandiflorum* and *Citrus Aurantium* on Hormone Experiment was conducted as follows in order to investigate the effect of a mixture of *Platycodon grandiflorum* and *Citrus aurantium* on the corticosterone level in the blood of depression-induced mouse or rat.

<4-1> Effect of Mixture of *Platycodon Grandiflorum* and *Citrus Aurantium* on Corticosterone Hormone of Depression-Induced Mouse Physiological saline was orally administered to C57/BL6 mice (male, 7-week-old) of a normal group and a stress control group, and 300 mg/kg of the mixture of *Platycodon grandiflorum* and *Citrus aurantium* was administered. Restraint stress was applied 2 hours later. After centrifuging blood taken from the depression-induced mouse, the corticosterone level in serum was measured by enzyme-linked immunosorbent assay.

Figure 6:
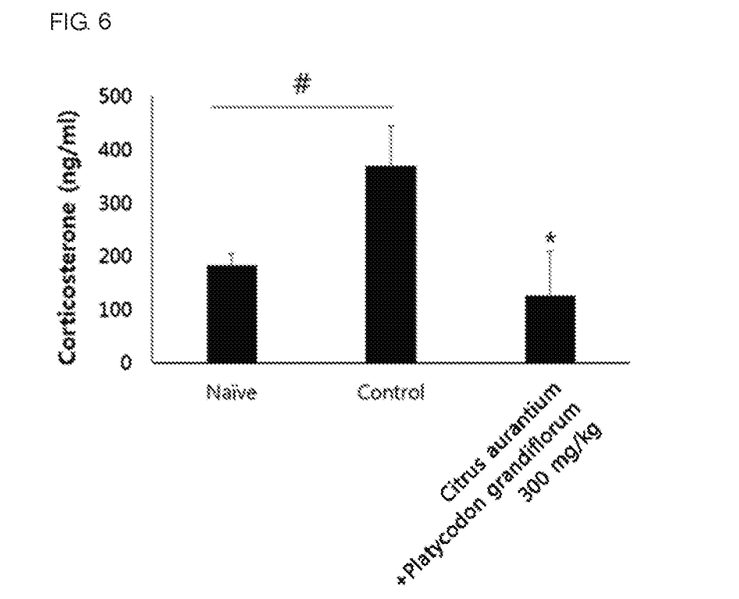
FIG. 6 shows a result of administering 300 mg/kg of a mixture of *Platycodon grandiflorum* and *Citrus aurantium* to a mouse with restraint stress-induced depression for 14 days and measuring the concentration of corticosterone in blood obtained on day 16 by enzyme-linked immunosorbent assay (#P<0.05 vs. na, *P<0.05 vs. control).

As seen from FIG. 6, it was confirmed that the stress control group showed increased blood corticosterone level, and the group to which the mixture of *Platycodon grandiflorum* and *Citrus aurantium* was administered showed decreased corticosterone level.

<4-2> Effect of Mixture of *Platycodon Grandiflorum* and *Citrus Aurantium* on Corticosterone Hormone of Depression-Induced Rat Physiological saline was orally administered to Wistar-Kyoto rats (WKY) of a normal group and a stress control group. After administering 10 mg/kg of amitriptyline, 300 mg/kg of SOCG, or 300 mg/kg of the mixture of *Platycodon grandiflorum* and *Citrus aurantium*, restraint stress was applied 2 hours later. Blood taken from the depression-induced rat was centrifuged and the corticosterone level in serum was measured by enzyme-linked immunosorbent assay.

Figure 7:
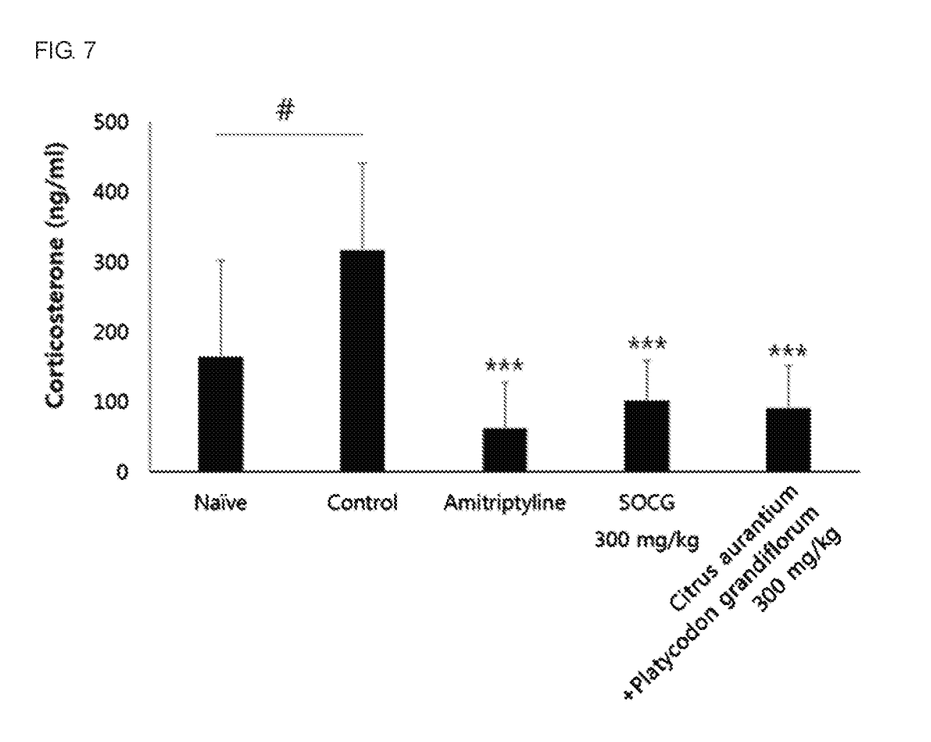
FIG. 7 shows a result of administering 10 mg/kg of amitriptyline, 300 mg/kg of SOCG or 300 mg/kg of a mixture of *Platycodon grandiflorum* and aurantii to WKY with restraint stress-induced depression for 14 days and measuring the concentration of corticosterone in blood obtained on day 16 by enzyme-linked immunosorbent assay (#P<0.05 vs. na, ***P<0.001 vs. control).

As seen from FIG. 7, it was confirmed that the stress control group showed increased corticosterone level in blood, whereas the group to which the SOCG mixture was administered and the group to which the mixture of *Platycodon grandiflorum* and *Citrus aurantium* was administered showed decreased corticosterone level. In addition, it was confirmed that the group to which the mixture of *Platycodon grandiflorum* and *Citrus aurantium* was administered showed a lower corticosterone level than the group to which the SOCG mixture was administered.

Through this, it was confirmed that the mixture of *Platycodon grandiflorum* and *Citrus aurantium* decreases the blood level of corticosterone, which is a stress hormone.

EXAMPLE 5

Effect of Mixture of *Platycodon Grandiflorum* and *Citrus Aurantium* on Neurotransmitters Experiment was conducted as follows in order to investigate the effect of a mixture of *Platycodon grandiflorum* and *Citrus aurantium* on the contents of neurotransmitters in a specific brain region of a mouse with stress-induced depression.

Physiological saline was orally administered to C57/BL6 mice (male, 7-week-old) of a normal group and a stress control group. After administering 200 mg/kg of a *Platycodon grandiflorum* extract, 200 mg/kg of a *Citrus aurantium* extract, 300 mg/kg of a mixture of *Platycodon grandiflorum* and *Citrus aurantium* or the tricyclic antidepressant AMT (amitriptyline) as a positive control to different groups, restraint stress was applied 2 hours later.

After harvesting the hippocampal region and the cortical region from the brain of the mouse with stress-induced depression, the tissue was homogenized and then centrifuged after mixing with perchloric acid. The concentration of the neurotransmitters, norepinephrine, epinephrine, dopamine and serotonin, in the obtained supernatant was measured by HPLC.

Figure 9:
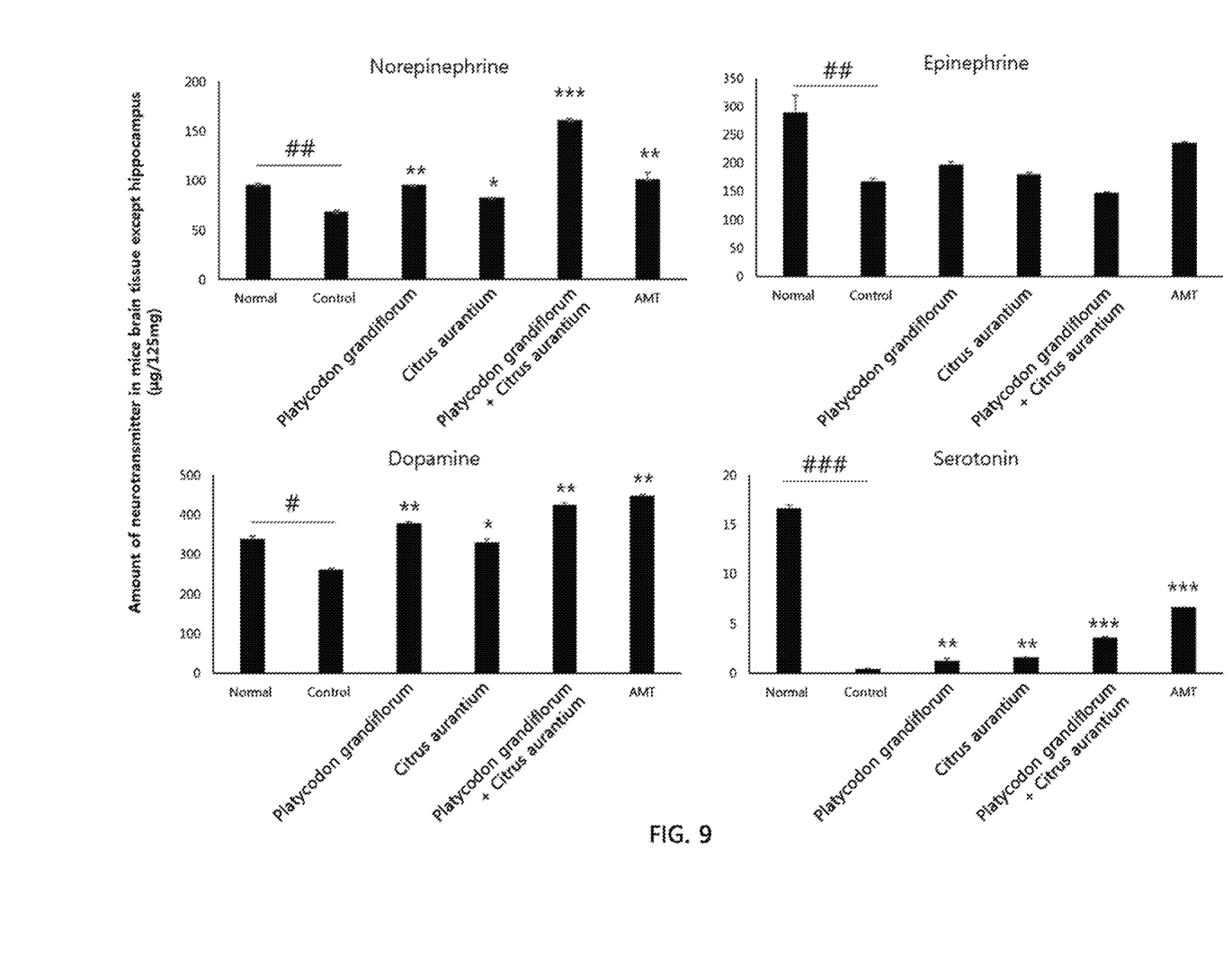
FIG. 9 shows a result of administering 200 mg/kg of a *Platycodon grandiflorum* extract, 200 mg/kg of a *Citrus aurantium* extract or 300 mg/kg of a mixture of *Platycodon grandiflorum* and *Citrus aurantium* to a mouse with restraint stress-induced depression and measuring the concentration of neurotransmitters in the brain excluding the hippocampal region by HPLC (#P<0.05 ##P<0.01, ###P<0.001 vs normal group (naive) *P<0.05 P<0.01, *P<0.001 vs control group).

As seen from FIG. 9, it was confirmed that norepinephrine, epinephrine, dopamine and serotonin were decreased in the cerebral region except the hippocampal region, for the control group as compared to the normal group. When the *Platycodon grandiflorum* extract, the *Citrus aurantium* extract or the mixture of *Platycodon grandiflorum* and *Citrus aurantium* was administered, the concentration of norepinephrine, dopamine and serotonin was increased as compared to the control group.

Figure 10:
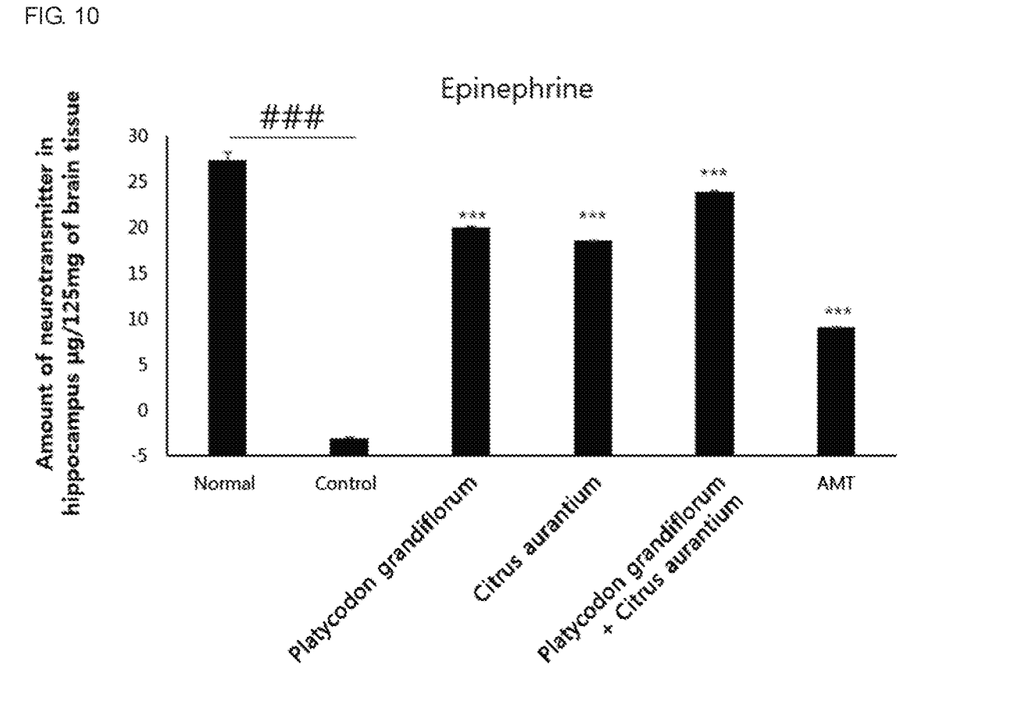
FIG. 10 shows a result of administering 200 mg/kg of a *Platycodon grandiflorum* extract, 200 mg/kg of a *Citrus aurantium* extract or 300 mg/kg of a mixture of *Platycodon grandiflorum* and *Citrus aurantium* to a mouse with restraint stress-induced depression and measuring the concentration of epinephrine in the hippocampal region of the brain by HPLC (###P<0.001 vs normal group (naive), ***P<0.001 vs test group).

In addition, as seen from FIG. 10, in the hippocampal region which is known as a region where cell death is induced by stress, epinephrine was significantly decreased in the control group as compared to the normal group. The concentration of epinephrine was increased when the *Platycodon grandiflorum* extract, the *Citrus aurantium* extract or the mixture of *Platycodon grandiflorum* and *Citrus aurantium* was administered as compared to the control group.

Through this, it was confirmed that the *Platycodon grandiflorum* extract, the *Citrus aurantium* extract and the mixture of *Platycodon grandiflorum* and *Citrus aurantium* is effective in inhibiting the decrease of neurotransmitters in the brain of a mouse with restraint stress-induced depression.

Accordingly, considering that the mixture of *Platycodon grandiflorum* and *Citrus aurantium* increases the level of norepinephrine, epinephrine, dopamine and serotonin, the effect of overcoming stress and inhibiting stress-induced cell death in the hippocampal region may be expected through their interaction.

EXAMPLE 6

Effect of Mixture of *Platycodon Grandiflorum* and *Citrus Aurantium* on Fatigue Experiment was conducted as follows in order to investigate the effect of a mixture of *Platycodon grandiflorum* and *Citrus aurantium* on the improvement of fatigue in a mouse with stress-induced fatigue.

<6-1> Expression of Genes Affecting Improvement of Fatigue

First, the known ingredients of *Platycodon grandiflorum* and *Citrus aurantium*, their effects and genes targeted by the ingredients were investigated, and experiment was conducted based thereon. While inducing depression of a mouse by applying restraint stress, a mixture of *Platycodon grandiflorum* and *Citrus aurantium* was administered for 14 days. On the last day of experiment, the mouse was sacrificed. After removing blood through cardiac puncture, the brain tissue was extracted. The extracted brain tissue was homogenized using TRIzol. After mixing with chloroform of the volume of 1/5 of the TRIzol, the homogenate was kept at room temperature for 3 minutes. Then, after centrifuging at 12,000 rpm and 4° C. for 15 minutes, the supernatant was taken and 2-propanol of the same volume was added. RNA was precipitated by conducting incubation at room temperature for 10 minutes. Subsequently, after centrifuging at 12,000 rpm and 4° C. for 10 minutes, the supernatant was removed and RNA pellet was washed with 80% ethanol. Then, after removing the supernatant by centrifuging at 7500 g for 5 minutes and spontaneously drying in the air, 50

μL of DEPC water was added and the mixture was stored at −80° C. The prepared RNA was subjected to microarray assay by BioCore.

As a result, a total of 33,793 genes were identified. Differentially expressed genes (DEGs) were screened from among them. Specifically, gene expression level was compared between the normal group and the control group, and gene expression level was compared between the control group and the group to which the mixture of *Platycodon grandiflorum* and *Citrus aurantium* was administered. The genes with the absolute value of log$_2$ (ratio of expression levels) being greater than 0.6 were screened as DEGs.

As a result, a total of 202 DEGs were screened, and signaling pathways that can affect the improvement of fatigue were identified based thereon. The result is shown in Table 1.

TABLE 1

| Substance | Exemplary compounds | All possible pathways |
|---|---|---|
| *Citrus aurantium* | (S)-Linalool | 65,662 |
| | Naringin | 16,770 |
| | Synephrine | 4,806 |
| *Platycodon grandiflorum* | Playtogenic acid A | 8 |
| | Platycodigenin | 890 |

<6-2> Pathways Affecting Improvement of Fatigue

The signaling pathways affecting the improvement of fatigue were analyzed based on the result of Example <6-1>.

Microarray assay was contacted using DNA obtained from a mouse to which a mixture of *Platycodon grandiflorum* and *Citrus aurantium* was administered. Based on the result, the gene expression level change ratio of the normal group and the control group, and the gene expression level change ratio of the control group and the group to which a mixture of *Platycodon grandiflorum* and *Citrus aurantium* was administered were derived. Recovery rate was designated for each pathway using the gene expression level change ratio. The recovery rate was determined to be closer to 0 as the gene expression level of the group to which a mixture of *Platycodon grandiflorum* and *Citrus aurantium* was administered is closer to the gene expression level of the normal group.

The total change ratio was calculated by summing all change ratios of gene nodes belonging to each pathway. For example, if a specific pathway is "compound→gene 1→gene 2→gene 3→depression" and the expression ratio of each gene is 0.3, 0.5, and 0.2 in order, the expression ratio of the pathway is 1.0. In this manner, the pathway change ratio of the normal group and the control group, and the pathway change ratio of the control group and the group to which a mixture of *Platycodon grandiflorum* and *Citrus aurantium* was administered were calculated. The recovery rate for each pathway was defined as follows.

Recovery rate=|(pathway change ratio$_{(normal\ group\ vs.\ control\ group)}$+pathway change ratio$_{(control\ group\ vs.\ group\ to\ which\ mixture\ of\ Platycodon\ grandiflorum\ and\ Citrus\ aurantium\ was\ administered)}$)/ (pathway change ratio$_{(normal\ group\ vs.\ control\ group)}$)|   <Equation 1>

For example, for a specific pathway, if the change ratio between the normal group and the control group is 4 and the change ratio between the control group and the group to which a mixture of *Platycodon grandiflorum* and *Citrus aurantium* was administered is 2, the recovery rate is 0.5.

As a result of measuring the recovery rate of the group to which a mixture of *Platycodon grandiflorum* and *Citrus aurantium* was administered, it was confirmed that, as the absolute value of the recovery rate is closer to 0, the DNA expression profile of the mouse to which a mixture of *Platycodon grandiflorum* and *Citrus aurantium* was administered is similar to that of the normal group. Based on this, from among the pathways expected to affect the recovery of the fatigue-improving genes, 15 pathways that recover the DEG expression level of the depression-induced mouse similarly to that of the control group were screened As show in Table 2, it was confirmed that the mixture of *Platycodon grandiflorum* and *Citrus aurantium* is associated with Casp3, Fos and BDNF in many pathways, from among the genes suspected with the disease. In addition, it was confirmed that the GOs associated with dopamine, epinephrine and norepinephrine are involved in the recovery from fatigue, as the node 4 of priorities 4, 5, 13, 14 and 15.

Through this, it was confirmed that the mixture of *Platycodon grandiflorum* and *Citrus aurantium* can improve stress-induced fatigue by promoting the expression of the genes affecting the improvement of fatigue.

TABLE 2

| Priority | Node 1 | Node 2 | Node 3 | Node 4 | Disease |
|---|---|---|---|---|---|
| 1 | MDM2 | MRPL43 | UBC | CASP3 | Depression |
| 2 | CDKN1A | HMGXB3 | UBC | CASP3 | Depression |
| 3 | KAT2B | VHL | UBC | FOS | Depression |
| 4 | MARCKS | ELAVL1 | GNB1 | GO:0007191[1] | Depression |
| 5 | FN1 | TUFM | SNCG | GO:0014059[2] | Depression |
| 6 | KAT2B | CTBP1 | CREBBP | FOS | Depression |
| 7 | HSPB1 | ZBTB1 | UBC | FOS | Depression |
| 8 | AKT1 | UBC | CASP8 | CASP3 | Depression |
| 9 | AKT1 | UBC | CASP8 | CASP3 | Depression |
| 10 | EGFR | ARF6 | UBC | FOS | Depression |
| 11 | EGFR | ETF1 | UBC | BDNF | Depression |
| 12 | FOS | UBC | LY6E | GO:0042415[3] | Depression |
| 13 | FOS | UBC | LY6E | GO:0048242[4] | Depression |
| 14 | FOS | UBC | LY6E | GO:0042415[3] | Depression |
| 15 | OGDH | PLSCR1 | EP300 | FOS | Depression |

[1]GO:0007191 = "Adenylate cyclase-activating dopamine receptor signaling pathway"
[2]GO:0014059 = "Regulation of dopamine secretion"
[3]GO:0042415 = "Norepinephrine metabolic process"
[4]GO:0048242 = "Epinephrine secret ion"

INDUSTRIAL APPLICABILITY

As described above, the present disclosure can be usefully utilized in preparation of a therapeutic agent for depression and anxiety, which are stress diseases, with few side effects using a natural product, and a health functional food effective in alleviation of depression and anxiety, which are stress diseases, and fatigue.

The invention claimed is:

1. A method for treating stress diseases wherein an effective amount of a pharmaceutical composition consisting of a *Platycodon grandiflorum* extract and a *Citrus aurantium* extract as effective ingredients is administered to an individual in need thereof,
    wherein a weight ratio of the *Platycodon grandiflorum* and the *Citrus aurantium* is (1-10):(1-10), and
    wherein the stress disease is one or more selected from the group consisting of depression, anxiety, and fatigue.

2. The method of claim 1, comprising administering 100 mg to 500 mg of the pharmaceutical composition per kilogram of body weight of the individual in need thereof daily.

3. The method of claim 2, comprising administering the pharmaceutical composition as a single dose.

4. The method of claim 2, comprising administering the pharmaceutical composition in multiple doses according to a fractionated treatment protocol.

\* \* \* \* \*